United States Patent [19]

Blaser

[11] 4,202,341
[45] May 13, 1980

[54] CARDIAC PACEMAKER CIRCUIT WITH VARIABLE OPERATION

[75] Inventor: Reinhard Blaser, Berlin, Fed. Rep. of Germany

[73] Assignee: Biotronik Mess- und Therapiegeräte GmbH & Co., Berlin, Fed. Rep. of Germany

[21] Appl. No.: 886,396

[22] Filed: Mar. 14, 1978

[30] Foreign Application Priority Data

Mar. 19, 1977 [DE] Fed. Rep. of Germany ....... 2712616
Mar. 19, 1977 [DE] Fed. Rep. of Germany ....... 2712617

[51] Int. Cl.² .............................................. A61N 1/36
[52] U.S. Cl. .............................................. 128/419 PG
[58] Field of Search ................ 128/419 PG, 421, 422, 128/423

[56] References Cited

U.S. PATENT DOCUMENTS

| | | | |
|---|---|---|---|
| 3,433,228 | 3/1969 | Keller, Jr. | 128/419 PG |
| 3,474,353 | 10/1969 | Keller, Jr. | 128/419 PG |
| 3,669,120 | 6/1972 | Nielsen | 128/419 PG |
| 3,926,197 | 12/1975 | Alley | 128/419 PG |
| 4,043,347 | 8/1977 | Renirie | 128/419 PG |

Primary Examiner—William E. Kamm
Attorney, Agent, or Firm—Spencer & Kaye

[57] ABSTRACT

An artificial cardiac pacemaker circuit producing heart stimulation pulses and arranged to operate in any selected one of a plurality of operating modes, the paths traversed by signals in the circuit being different in each operating mode, the circuit including a stage emitting pulses having a predetermined duration and amplitude and/or repetition rate, a stage arranged to actuate further signals during at least a first operating mode in response to such pulses, and a stage operative only during a second operating mode to actuate or suppress such signals at the end, or for the duration, of each pulse in order to at least indirectly fix the time position of each stimulation pulse.

26 Claims, 8 Drawing Figures

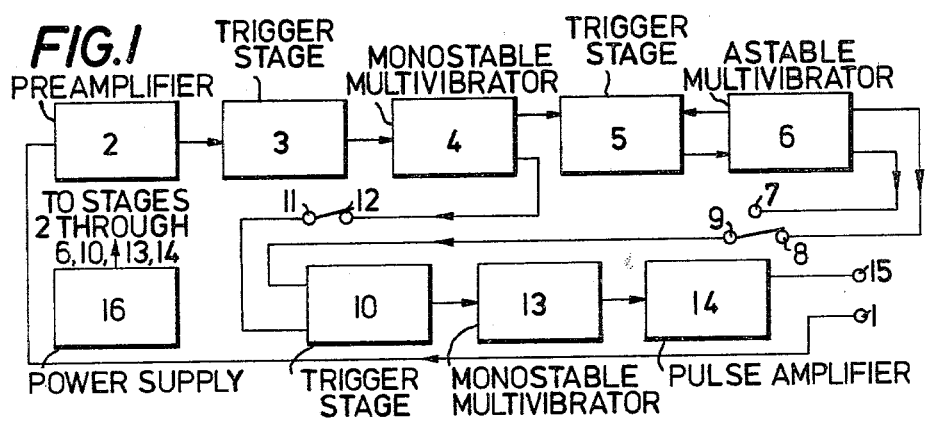
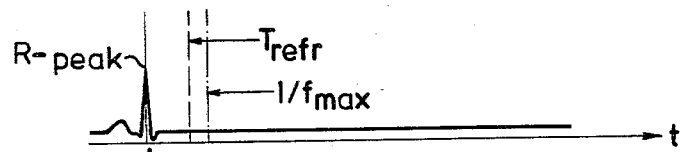
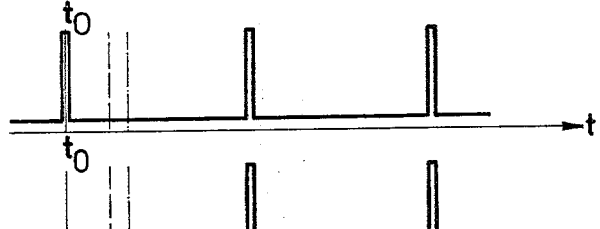
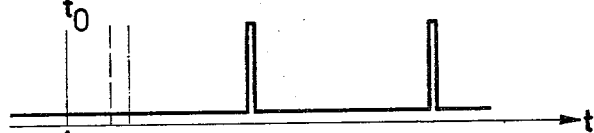
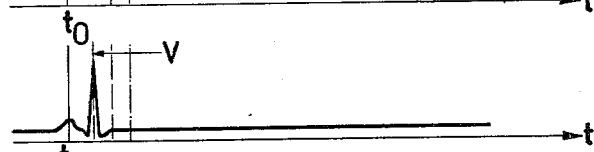
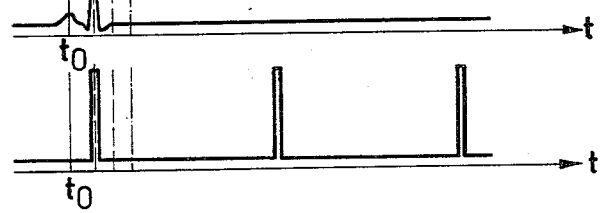
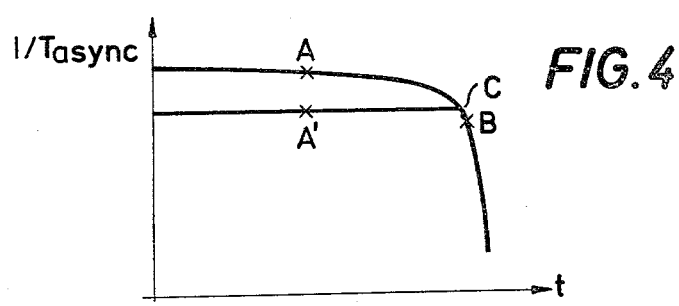

CARDIAC PACEMAKER CIRCUIT WITH VARIABLE OPERATION

BACKGROUND OF THE INVENTION

The present invention relates to a circuit for an artificial, in particular implantable, cardiac pacemaker which is suitable for different modes of operation.

Artificial pacemakers are known which in cases of heart weakness or disorders in the natural heart rhythm take over the stimulation of the heart and take care that in spite of the presence of a pathological defect in the area of the natural function control of the heart it will be able to perform its life sustaining task.

Such pacemakers include those of the demand-mode type in which the time duration of such pulses is preferably determined by the refractory period, and those of the auricle controlled type in which the time duration is determined by the P-Q delay. The refractory period is that period of time during which no stimulation pulse is actuated, even if an input signal should appear. The P-Q delay is the period of delay, which corresponds to the transit time of the physiological excitation from the auricle to the ventricle.

The life of a patient depends to a decisive degree on the orderly operation of the pacemaker. It must be assured that the device is continuously operable under any conditions without external access for the longest possible time.

Interruption in the operation of a pacemaker may occur, in principle, as a result of two different causes:
1. by malfunction due to the unpredictable failure of any component;
2. by exhaustion of the source of energy.

The former type of interruption occurs unexpectedly, so that it leads to a dangerous situation for the patient which must be avoided under all circumstances. Efforts have therefore been made to make the reliability of the circuits used in pacemakers so great that the risk of unexpected failure is reduced practically to zero. Reliability factors have been attained which exceed the values required in space science.

In order to further reduce the risk of failure, it has been attempted to design the circuitry employed so that failure of a single component cannot lead to complete malfunction of the entire device or so that the impending failure of a component will become evident in time by a change in the operating parameters of the device.

The realization of high reliability, i.e. dependable assurance against unexpected operating malfunctions, involves considerable expenditures since the selection of components and the controls imposed during various manufacturing stages must be effected with extreme care.

The probability of an unexpected malfunction in operation generally increase with the length of time during which the device has been in use. At a certain point in time, therefore, the operating dependability of the pacemaker has decreased to such a point that the required reliability is no longer assured. Thus usefulness of the device has come to an end.

This point in time depends not only on the increase in the statistical failure rate but also on a number of predictable events, such as the attack of body fluids on the housing and the deterioration of its properties due to aging of the components. Through the use of high quality materials and components it is today possible to secure many years of proper operation from an artificial pacemaker. It has been found that an increase in the operating dependability generally also leads to an increase in its expected service life and thus its possible period of use, since both values are linked together.

The second group of operating malfunctions presents a lesser risk for the patient since the exhaustion of the energy sources occurs at regular intervals and can be determined in time by appropriate measuring devices. Even an unscheduled premature exhaustion of an energy source can be determined by check-up examinations which can take place at long intervals because the period of time between the first sign of reduction in the performance of the energy source and its final failure is generally sufficiently long. It is, of course, desired to make the operating life of the energy sources in implantable pacemakers as long as possible since a change in energy source always requires explanation connected with surgical procedure which should always be performed as rarely and at as long intervals as possible in each case.

Presently the energy sources for implantable artificial pacemakers are preferably primary chemical elements whose service life, which depends on the current consumption of the electrical pacemaker circuit employed, is at least several years. For the recently employed lithium silver chromate elements, the expected service life is already about 8 to 9 years. For economic reasons, the possible life of the pacemaker should be at least equal to, and preferably greater than, the maximum period of operation of the batteries.

In addition to longer service life, lithium silver chromate elements have the additional advantage of a greater energy density compared to the mercury oxide zinc elements which were previously used most commonly. The potential of two to three volts of the lithium elements is above the values of the primary elements which were previously used most frequently. Since, however, to promote greater redundancy which decreases the chances for failure, it is preferred to connect the lithium cells in parallel instead of in series as was previously done, there is in the end less potential available to supply the pacemaker circuit with current. The previously employed circuits have the drawback that they have poorer operating characteristics at lower supply potentials than they have at higher potentials.

It is thus obvious that the existing requirements led to the development of devices in the pacemaker art which meet the highest demands with respect to expected service life and reliability but which do involve considerable expenditures.

Pacemakers offer decisive advantages over treatment with medications and in order to allow pacemakers to be even more broadly applicable, there exists the need to reduce the costs of manufacture and use without reducing the level of the operating requirements which they must satisfy.

One development in this direction, to reduce the costs of use of pacemakers, involves making the pacemakers to be reusable. Experience has shown that pacemakers are predominantly implanted in patients who are already at an advanced age or those whose heart damage coincides with other organic damage. Thus it may happen that the probable service life of the pacemaker exceeds the life expectancy of the patient. It has therefore been made possible, in principle, to reuse a pacemaker after disinfection, i.e. to implant it in another patient. Since, however, the pathology connected with heart rhythm disorders varies from one person to another, there often exists the necessity to adapt a pacemaker, before it is reimplanted, to the particular requirements of the new user unless there exists a store of a large number of devices meeting the large variety of different pathological symptoms.

It also happens that the pathological behavior of the heart of one and the same patient changes in the course of time requiring a corresponding modification of the operating parameters of the pacemaker. Thus, for example, the threshold value of the heart may change with time. The likelihood that such a change will occur and that the pacemaker must be adapted to it increases with the length of time the device is implanted in a patient to stimulate his heart. Therefore, the necessity of having to change one or more of the operating parameters will occur more frequently the longer the pacemaker has been in service.

Such adaptation of operating parameters to changes occurring in the patient may be effected, for example, at the time of the explanation which is in any event required to permit battery replacement. It is also possible, however, to adjust the mode of operation of a pacemaker while it is in the implanted state, by means of remote control. If means for subsequent variation of the operations parameters of a pacemaker are not provided, it will be necessary for the patient, if his pathological symptoms change, to receive a new device before the maximum service life of his old device has been utilized.

Pacemakers of uniform types which can be adapted to various types of heart rhythm disorders can be produced more economically and with lower operating and storage costs than a plurality of different types of devices. Since manufacturing costs represent a high proportion of the total costs of a pacemaker, a reduction in such costs can significantly reduce a patient's expenses.

German Offenlegungsschrift [Laid-open Application] No. 2,163,482 discloses a pacemaker circuit which permits fixing of the heart threshold value without surgical procedure. The procedure circuit is associated with switching mechanisms which permit remote setting of the amplitude of the pacemaker output in dependence on the heart threshold value determined by the physician. In the pacemaker circuit described in the above-mentioned application it is possible to subsequently adapt the device to a changed threshold value of a patient but it is not possible to subsequently adapt it to changes in the basic pathological symptoms which would require, for example, a transition from negative R wave control to positive R wave control. Additionally, that circuit does not permit of a reduction in production costs since a variation of the output voltage of the pacemaker, as required upon a change in the threshold voltage of the heart, can be accomplished simply by changing a few resistance values so that no need exists for a completely new circuit design.

SUMMARY OF THE INVENTION

It is an object of the present invention to enable a cardiac pacemaker to be set to different modes of operation, for treating various types of heart rhythm disorders while operating at as optimum a setting as possible in each mode of operation.

A further object is to meet the demands imposed on a pacemaker circuit individually for each mode of operation.

A further object is to use, as much as possible, all components provided in the circuit during each mode of operation, i.e., the mode of operation is changed by altering switching connections so that all individual components remain in operation in order to produce certain operating states.

The invention additionally provides a circuit for a cardiac pacemaker which, even at lower voltage potentials, has a very low current consumption and assures the highest possible operating reliability even in the face of interferences, fluctuations in operating parameters and the like. Moreover, operation is possible also with voltage sources having a higher potential and a reliable indication is obtained regarding the impending end of operability of the energy source employed. The circuit processes signals with the same dependability when the voltage potential of the primary elements employed has dropped as it did at the start of its service life.

These and other objects are achieved according to the present invention, in an artificial cardiac pacemaker circuit constructed to produce heart stimulation pulses and to operate selectively in any selected one of a plurality of different operating modes, which include a first operating mode in which signals traverse first signal paths through the circuit, by constructing the circuit to be operated selectively in a second operating mode in which the signals traverse paths differing from the first paths, and by providing the circuit with means connected for emitting pulses of a predetermined duration and amplitude and/or a predetermined repetition rate, means connected for producing additional signals during operation in at least the first operating mode in response to the emission of pulses by the pulse emitting means, and means connected for actuating or suppressing signals in the circuit only during operation in the second operating mode at the end, and/or for the duration, of each pulse emitted by the pulse emitting means, in order to at least indirectly fix the time position of each stimulation pulse produced by the circuit.

In at least one first mode of operation, pulse emitting stages generate a train of pulses or shape pulses with respect to their width or amplitude. In at least one second mode of operation, the width, or the instant of occurrence of the leading or trailing edge, of each such pulse is additionally used to control the actuation of the heart stimulation pulses provided by the pacemaker.

The present invention, in order to provide a cardiac pacemaker circuit which is suitable for a wide range of conditions, employs a uniform circuit design which provides for various modes of operation.

The development of a cardiac pacemaker circuit is a highly complex process due to the extreme requirements that must be met. Since it may happen that a solution which is the best in one respect is incapable of meeting another requirement completely, it is always necessary to conduct extensive tests.

The requirement of utmost operational dependability coincides with endeavors to keep current consumption as low as possible in order to increase the service life of the energy source.

Another requirement is that the operating parameters be as constant as possible. Since the individual components and groups of components interact with one another, it is impossible to design the individual function blocks of a pacemaker circuit independently of one another. The mode of operation, operational reliability and current consumption are dependent on one another in such a way that it is often impossible to obtain the absolutely best results in all respects. Often it is necessary to settle for the optimum attainable solution.

In the endeavors to create a circuit that can be used for various modes of operation there exists the additional difficulty, however, of maintaining the required conditions for each one of these modes of operation and for differently set circuit parameters.

Seen from this point of view the circuit according to the invention provides considerable advantages.

Thus, in the circuit of the invention the setting for the different modes of operation can be effected by simply switching in or changing line connections.

Due to the possibility of definitely separating components which determine pulse frequency from those which effect pulse shaping and determine pulse width, it is possible to obtain high stability of the mode of operation of the circuit even when changes occur in external operating conditions. Such circuits continue to operate in a stable manner even if the operating voltage drops or is low.

One of the significant features of the present invention is that pulse shaping means, i.e. means for obtaining a sufficient pulse width, are used in all modes of operation. In some modes of operation, these means are utilized in multiple ways so that the duration of the pulse can also be used to perform a logic function.

Similarly, the time duration of the pulses generated by a circuit for emitting a certain pulse rate can be additionally utilized in some modes of operation, in that the generation of stimulation pulses for the heart is additionally influenced by the time position of the beginning and end of the pulses or their time spacing, respectively, this time position being utilized in some modes of operation for causing a time-delay of the pacemaker's input with respect to its output or a refractory period for which no output will occur as response to an input.

Due to the fact that a sufficient pulse width is maintained even in modes of operation in which a certain time duration of the generated pulses is not required, the circuit operates particularly dependably and the stages are well decoupled from one another.

According to a preferred embodiment of the invention, the problem of providing an energy saving circuit design is solved in an economical manner in that means are provided to give the pulses as steep a switch-off edge as possible in a pulse output stage in which the time duration of the pulses is controlled by a monostable multivibrator circuit.

Special circuit means also make it possible to design the separate means for frequency generation in an advantageous manner so that a defined drop occurs in the generated frequency when a given operating voltage is no longer being reached. This makes external monitoring of the aging state of the battery possible.

Other improvements according to the invention are based on recognition that a series of instability factors appearing during operation of the pacemaker originates in the influence one circuit component has on another in the complex superposition of the behavior of the components under different operating conditions. By separating the functions and performing them in different components, decoupling is realized which makes it possible to use the circuit down to extremely low operating voltages, while also giving rise to a series of other possibilities. For example, since only one component performs a special function, the operating behavior of this individual component can be improved directly and controlled. The individual components may also perform other functions of subordinate significance and a change in these other functions upon a change in the external conditions does not have as extensive an effect as a reduction in the main function of the component. Leads coming out of the circuit are provided to easily connect the individual components together in various ways for different modes of operation of the pacemaker circuit since possible retroactive effects between the individual circuit components are reduced when the components are interconnected in such manner.

It is therefore possible to design a cardiac pacemaker circuit which is suitable for universal use not only with respect to the energy sources to be employed but also with respect to the various possible modes of operation.

BRIEF DESCRIPTION OF THE DRAWINGS

FIG. 1 is a block circuit diagram of a preferred embodiment of a cardiac pacemaker circuit according to the invention.

FIGS. 3a–3e are diagrams illustrating the waveforms of signals in the circuit during various modes of operation.

FIG. 4 is a diagram illustrating the dependency of one operating parameter on the service life of a pacemaker.

DESCRIPTION OF THE PREFERRED EMBODIMENTS

Figure 2:
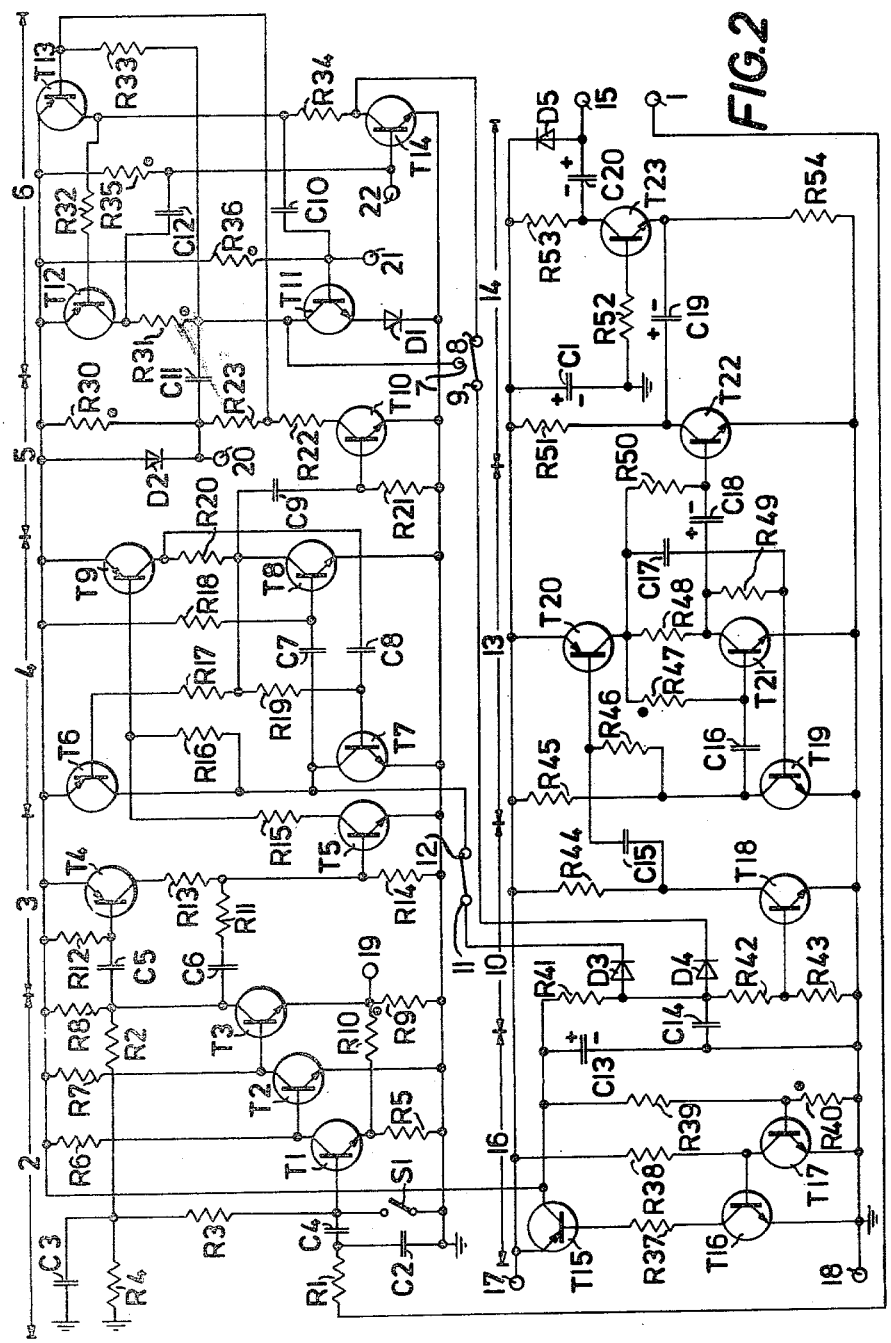
FIG. 2 is a detailed circuit diagram of one advantageous form of construction of the individual components of the pacemaker of FIG. 1.

FIG. 1 is a block circuit diagram of a preferred embodiment of the cardiac pacemaker according to the invention, in which an input signal from an electrode (not shown) which has been surgically implanted in the heart of a patient is fed to a preamplifier 2 via a terminal 1. In this preamplifier the level of the input signal is raised and its frequency curve is shaped, if required, according to the individual therapeutical needs by varying the pass-band characteristics determined by the time-constants of R2, R3, R4, C3 (T-filter); R1, C2 C4 and C6, R 11.

The output signal from the preamplifier 2 is fed to a trigger stage 3. A particularity of this trigger stage is that it emits an output pulse upon receipt of an alternating voltage pulse of either polarity. This output pulse constitutes the input signal of a monostable multivibrator 4 which serves to shape the pulses from stage 3 and emits a rectangular output pulse at each of two outputs when it receives a pulse from trigger stage 3. The pulse at each output of multivibrator 4 is of given duration and the pulses at the two outputs are of respectively opposite polarities.

The pulses, of a first polarity, at one output of multivibrator 4 are fed to a further trigger stage 5 which acts to limit the upper limit frequency of the trigger pulses. At the output of trigger stage 5 a circuit is additionally provided which prevents a trigger pulse from being effective if it occurs before a given refractory period has elapsed following a preceding pulse. One embodiment of such circuit will be described below.

The signal emitted by trigger stage 5 synchronize an astable multivibrator 6. If this multivibrator is not triggered, it emits pulses at the asynchronous basic rate of the pacemaker circuit. The pacemaker's operation is "asynchronous" then with respect to the frequency of the patient's heart beat. The repetition rate is determined substantially by one of two timing members included in the circuit of the astable multivibrator. For the actuation of the subsequent stages of the pacemaker, the shape of the pulses emitted by multivibrator stage 6 is of no significance. However, the point in time at which the pulse edges occur is of significance and is employed to assure that actuation of subsequent states occurs precisely at defined points in time.

The width of each pulse emitted by astable multivibrator stage 6, i.e. its time duration, serves, depending on the selected mode of operation of the circuit, to control directly, or with a delay, subsequently connected circuit groups. This makes it possible to generate, for auricle controlled cardiac pacemakers, a representation of the period of delay which corresponds to the transit time of the physiological excitation from the auricle to the ventricle of the heart in the circuit which serves as the frequency determining element for the asynchronous basic rate.

Thus a group of components contained in the circuit, which is required in principle for every mode of operation, is utilized for an additional function in one or a plurality of other modes of operation. This makes possible creation of a uniform production line for cardiac artificial pacemaker circuits in which certain circuit components are not superfluous in individual modes of operation. In each mode of operation these components perform at least one basic function and in other modes of operation they may be assigned additional functions. For modes of operation in which only the basic function is utilized, the circuit is designed so that all groups of components can perform this function in an optimum manner, i.e., with the greatest stability, even if there are fluctuations in parameters. Circuit portions which in individual modes of operation are not fully utilized always contribute to the total operation of the circuit, if only with increased redundancy, which constitutes an additional safety factor against operating malfunctions.

When it receives an input signal from stage 5, the astable multivibrator 6 directly emits an output signal if the pacemaker is effecting a ventricle controlled operation. If it operates under the control of the auricle, however, pulse emission occurs only after a fixed delay period.

The astable multivibrator circuit 6 is thus caused to always emit a pulse as a result of a signal received from the heart and this emission of pulses is continued in the rhythm of the basic rate if no further pulses are received from the heart which are sufficient to activate the trigger stage 3. The undelayed and the delayed signals from the astable multivibrator 6 are fed to connecting points 7 and 8, respectively, through separate output lines.

Depending on the presently selected mode of operation of the pacemaker circuit, one or the other of these connecting points 7 and 8 is connected with a connecting point 9 so that a selected signal from multivibrator 6 is fed to a trigger stage 10 which has at its input a logic circuit that will be described in detail below. Either one of connecting points 7 and 8 may be permanently connected to connecting point 9 during manufacture of the pacemaker, or switching means may be provided which make it possible to change the mode of operation of the pacemaker by switching the line connections when the pacemaker is either in the explaited or implanted state. Such switching means can be capable of being actuated, if required, by remote control effectuated through the pacemaker housing or through the housing and the body of the patient, switching means of this type being well known to persons skilled in the art.

The selected output signal thus travels from connecting point 9 to one input of trigger stage 10. In the case of synchronous operation of the pacemaker circuit, this trigger stage, when actuated, directly emits an output pulse for the pacemaker circuit to stimulate the heart. If the pacemaker is operated in the demand mode, however, there will be no output pulse when a natural heart reaction is present. This function is controlled by logic switching means and signals supplied from a connection point 11 to a second input of stage 10.

In the demand mode, connecting point 11 is connected with connecting point 12, in the manner described above with regard to connecting points 7 to 9. The monostable multivibrator 4 which in synchronous operation serves only to generate a pulse of defined width and amplitude, is used in the demand mode additionally to block the input of trigger stage 10 for a certain period of time, i.e. to make it unreceptive for a signal coming from the astable multivibrator 6 during such period of time. Whereas during synchronous operation of the pacemaker monostable multivibrator 4 generally contributes to an increase in stability of operation in that it assures safe actuation of the subsequent stages, in the demand mode the multivibrator time constant is utilized for an additional purpose in circuits according to the invention.

When designing such a circuit, the initial desire is to meet the more difficult of the demands placed on the circuit by the different conditions. In the extreme case, this may only have the result that, in certain modes of operation of the circuit, the capabilities of the individual circuit components are not utilized fully. On the other hand, security against malfunction is increased in many cases. In the present case, the time constant, or pulse duration, of the monostable multivibrator 4 will be selected so that it is sufficient to permit a pulse of sufficient duration to actuate the astable multivibrator 6 via trigger stage 5, as well as to inhibit input of trigger stage 10 for a sufficiently long period of time.

The output signal from trigger stage 10 serves to actuate a further monostable multivibrator 13 which effects pulse shaping with respect to the output signal produced by the pacemaker circuit. By separating the means for determining the shape of the output pulses from those for fixing the time at which they occur, the stability of the entire circuit arrangement can be increased further. Added to this is the possibility of separately influencing the separate stages during the various modes of operation of the circuit. This can also be done by changing the value of individual components, possibly by connecting additional components in parallel or by supplying additional electrical signals. In any case the range of variation of the circuit parameters than can be realized by change or influence is far greater than if the two functions, pulse frequency and pulse duration, were determined by one and the same component. The increased dependability of the circuit is evidenced, for example, by its increased resistance to changes in operating voltage. Additional means are provided at the output of the monostable multivibrator 13 to increase the slope of the trailing edge of the pulse emitted by this stage. Details of embodiments of all these circuits will be described below.

The output signal from trigger stage 13 reaches a pulse amplifier stage 14 in which the voltage of the output signal from stage 13 is doubled. The amplified signal is fed to an output terminal 15, from where it is fed to an electrode (not shown) implanted in a patient's heart.

In the case of a ventricle controlled operation of the pacemaker circuit, the output terminals 1 and 15 are connected together and to a common electrode. A voltage is produced between this electrode and a further electrode which is at the ground potential of the pacemaker circuit, this ground, or reference, electrode being constituted, for example, by the housing of the pacemaker.

An additionally provided current supply circuit 16 contains a voltage regulator connected to supply stages 2 to 6 of the pacemaker circuit with a fixed voltage which is reduced with respect to the battery voltage. The output stages 10 to 14 receive the full battery voltage.

Due to the fact that the components responsible for the time of the emission of stimulation pulses are supplied with a lower regulated voltage, it is possible to additionally secure this part of the circuit, which like the entire circuit is also designed for operation at lower operating voltages, against changes in the supply voltage and to assure maintenance of precise time positioning for the pulses under any circumstances, if possible. This provides an additional security against changes in the parameters of components due to aging or the like.

A particular advantage of regulating the operating voltage only for those circuit portions which determine the point in time of the stimulation pulse is that the power loss occurring at the regulating member is small because the supply of the power stages is not included in the regulation. Due to the fact that the component for fixing the duration of the stimulation pulses is separated from those circuit portions which determine if and when a pulse is emitted and is not supplied with a regulated voltage but with the unregulated battery voltage, the latter voltage can be directly used to actuate the final stage with full utilization of the available battery potential.

The versatility of the circuit according to the invention, resulting from its universal applicability with different types of batteries, is realized in that the circuit is designed for the lowest suitable supply voltage and still assures sufficient safety if the battery voltage drops even further. This is realized by the above-mentioned measures to assure safe operation at low battery voltages. Universal adaptability is offered, in particular in that the asynchronous fundamental frequency of the pulses for normal operation with a fresh battery is adjustable separately from the rate resulting for a borderline region of operation with increasing exhaustion of the battery so that this state is indicated to the physician. In the illustrated circuit, regulation of the operating voltage sets the fundamental frequency so that it is maintained as long as the battery voltage lies above the regulated voltage value. The borderline rate is set for a voltage value which occurs when the regulating effect has ceased so that the steeper drop of the supply voltage in this region results in a greater change of frequency.

FIG. 2 shows details of one advantageous circuit arrangement of the function blocks shown in FIG. 1. The preamplifier 2 includes d.c. coupled transistors T1, T2 and T3. The total voltage amplification of the preamplifier is set via resistors R8 and R9 as well as R5 and R10. Capacitors C2 and C4 determine the lower and upper limit frequencies, respectively, of the preamplifier circuit. A switch S1 is provided to short circuit the input of the amplifier in order to prevent triggering of the pacemaker by input pulses. The other illustrated components of preamplifier 2 perform conventional functions.

The trigger stage 3 receives the output signal from the collector of transistor T3 of preamplifier 2 via capacitors C5 and C6. The signal from capacitor C6 is supplied to stage 3 via resistor R11, while the signal from C5 is inverted by a transistor T4, and the inverted signal is fed via a resistor R13, to a resistor R14 where it is superposed on the signal supplied via resistor R11 to produce a combined signal which controls a transistor T5. With appropriately dimensioned components, i.e. with resistors R11 and R13 large enough with respect to the output resistances of transistor stages T3 and T4, the pulse amplifier stage including transistor T5 is actuated in response to both polarities of the input signal at terminal 1. This assures, on the one hand, that changes in potential of both polarities across the electrode are processed and, on the other hand, triggering is simultaneous for both polarities, i.e. without delaying signals of the one polarity relative to the other. Changes in the operating parameters as a result of changes in the circuit parameters for signal paths associated with different polarities are thus excluded.

The output signal at the collector of transistor T5 actuates the monostable multivibrator circuit 4 via a transistor T9 which is provided in the collector branch of a transistor T8 in place of a load resistance. The multivibrator circuit proper is constituted by transistor T8 and a further transistor T7 having a transistor T6 connected in its collector branch in place of a collector resistor. Such circuits have the advantage of using little current since a transistor, as opposed to a fixed operating resistor, may take on an infinitely high ohmic resistance value in the nonconductive state. The complementary pairs of transistors T8-T9 and T7-T6 each form a push-pull system the individual transistors of which are alternatingly conductive and blocking. The time constant, or pulse duration, of the monstable multivibrator circuit is fixed by the values of a capacitor C7 and a resistor R18.

Monostable multivibrator 4 produces pulses of defined amplitude and time duration, each such pulse having been derived from the undefined biological signal. These pulses travel via a coupling capacitor C9 to the input of a transistor T10 which forms a switching amplifier in trigger stage 5. The coupling capacitor C9 is dimensioned so as to permit transmission of pulses from the output of stage 4 only up to a selected maximum rate, preferably having a value of between 3 and 5 Hz and representing the maximum rate at which pulses are to be processed by trigger stage 5. If pulses appear at the output of stage 4 in a faster sequence, the time between the pulses is no longer sufficient to sufficiently discharge capacitor C9 so that the transmitted pulses are not of sufficient amplitude to switch through transistor T10. Whenever monostable multivibrator 4 generates pulses at a rate higher than the maximum, the pacemaker circuit changes to emission of pulses at the asynchronous basic rate, which is safer for the patient and which, as a result, corresponds to operation that is actuated when no pulses at all are amplified by preamplifier 2.

While the capacitor C9 prevents processing of pulses occurring at a rate exceeding a certain upper repetition frequency, further means are provided in the collector branch of transistor T10 to prevent signal emission in response to a pulse which appears at a short interval after another pulse, i.e. the second of a pair of double pulses. Thus the pacemaker circuit is insensitive to signals, i.e. is refractory, for a certain period of time after the occurrence of an input pulse, a time that may be, for example, between 230 ms and 400 ms.

This refractory period is produced in that during triggering of the subsequent astable multivibrator 6, the latter couples a signal back to a capacitor C11 in stage 5, thus charging that capacitor and blocking the input of the multivibrator for a certain period of time.

This process takes place as follows: upon occurrence of a pulse, transistor T10 is switched through, thus actuating a transistor T13 of multivibrator 6. This blocks transistor T12 and switches through transistor T11. Capacitor C11 is thus charged. If the astable multivibrator circuit flips back to its starting state after some time, the transistor T12 becomes conductive again while transistor T11 blocks. The potential at that terminal of capacitor C11 which is connected to diode D2 is now pushed beyond the positive regulated supply potential. Therefore, capacitor C11 must now discharge via resistor R30 since diode D2 is blocking. With the appropriate dimensioning of resistors R22 and R23, transistor T13 can now be actuated via transistor T10 for the refractory period since even if transistor T10 is switched through, the potential across the base of transistor T13 is not sufficiently negative with respect to its emitter voltage to permit actuation. The duration of the refractory period itself may be changed by varying the value of resistor R30.

In the illustrated pacemaker circuit it is of particular significance that those components whose value changes with different modes of operation, i.e. adjustment of sensitivity, pulse widths and the like, are arranged so that their terminals are either at ground potential or at the positive supply potential. This makes it possible in a particularly simple manner to change those values by means of parallel or series connections, possibly also by remote control, since the number of leads to be brought out of an encapsulated circuit is to be kept at a minimum.

The circuit for limiting the upper frequency rate of the pulses to be processed and for suppressing double pulses exhibits the advantages of the circuit according to the invention with particular clarity. Due to the fact that exact pulse shaping with respect to pulse width and amplitude is assured in every mode of operation, defined capacitor recharges occur in the circuit around transistor T10 so that the discharge periods are constant as well. Those periods can thus be utilized directly in the circuit for effecting time determinations, regulation or the like without requiring additional monostable multivibrator circuits or the like. At the same time, as shown, the pulse shaping elements provided for other modes of operation can additionally take over the control of groups of components by performing a defined emission of signals at certain points in time, or having certain time durations, etc.

The astable multivibrator circuit 6 contains, similarly to the monostable multivibrator circuit 4, additional complementary transistors T12 and T13 each connected in the collector branch of a respective one of transistors T11 and T14. The time constants of circuit 6 are determined by the values of the series resistor-capacitor combinations R36/C10 and R35/C12. The time constant defined by the combination R35/C12 is much smaller than that of the combination R36/C10. The repetition rate of the pulses produced by circuit 6, when operating astably, is thus determined mainly by R36/C10. In the present pacemaker circuit, combination R35/C12 preferably serves to shape the pulses, i.e. to assure that the pulses emitted by circuit 6 are sufficient in amplitude and duration during all modes of operation to activate subsequent stages and assure stable operation.

The time difference between the leading and trailing edges of each generated pulse is utilized only in a further mode of operation of the device, i.e. in the auricle controlled operation, to effect a time delay between triggering of the multivibrator circuit 6 and actuation of a heart stimulation signal. Since the subsequent stages are triggered by an edge of each pulse, it is only necessary, as shown, to switch the connection of terminal 9 between connecting points 7 and 8 to realize delayed signal emission.

During each triggering, astable multivibrator 6 is returned to its starting state by trigger stage 5. This effects immediate signal emission at connecting point 8 and a signal emission at connecting point 7 which has been delayed by the blocking time of transistor T14, determined by the time constant of combination C12/R35, the "signal" here being understood to mean a pulse edge constituting a voltage change in a given direction, or of a given polarity.

If astable multivibrator 6 is not triggered, pulses are emitted regularly in the rhythm of the fundamental frequency, or repetition rate, which, as mentioned above, is essentially determined by the time constant of combination C10/R36. The pulse repetition period is constant over a broad range of supply voltage levels.

In order to make a further drop in the operating voltage within a minimum range externally determinable in an implanted cardiac pacemaker, means are provided to cause this voltage drop to become apparent by creating a drop in the fundamental frequency of the astable multivibrator. For this purpose, a silicon diode D1 with a forward voltage drop of between 0.4 and 0.7 volt is connected in the emitter path of transistor T11 to raise the emitter voltage so that a change already occurs with respect to the time constant of combination R36/C10 before any other time constants of the multivibrator stages are influenced thus assuring constant cooperation.

The voltage-frequency characteristic of multivibrator 6 may be freely set within wide limits by appropriately dimensioning the individual components. Particularly significant in this connection is the fact that the frequency can be set in a defined manner for two different voltage values: on the one hand, by selecting the time constant for the operating range at the normal, almost constant, operating voltage; and on the other hand, by selecting the forward voltage drop of the diode D1, in the region of the steep drop occurring in the battery voltage at the end of its service life, below the value at which current supply circuit 16 no longer has any regulating effect.

The selected output signal of the astable multivibrator 6 is fed from terminal 9 to trigger stage 10 which contains a transistor T18 whose base is connected to receive such signal. Transistor T18 is actuated by positive input signals, i.e. whenever the voltage at its base is not held in the vicinity of ground potential by the action of a diode D3 or D4. Thus it is possible to inhibit the actuation of the output stage via diode D3, as mentioned above. If in the demand mode of operation the connecting points 11 and 12 are connected together, the occurrence of an action potential originating from the heart itself will block, by the operation of monostable multivibrator 4, the input of trigger stage 10 for the duration of the pulse emitted by that monostable multivibrator. This blocking of trigger stage 10 is an additional function performed by the multivibrator stage 4 which is utilized only in some modes of operation and is derived in an advantageous manner from the characteristic of the circuit that pulses of a given width and amplitude, which are required to generate defined operating states, are present at the output of the multivibrator stage 4 in any case.

The output signal at the collector of transistor T18 triggers, via a capacitor C15, the monostable multivibrator 13 which is constructed in a known manner and, in contradistinction to the multivibrator circuits 4 and 6, includes a complementary switching transistor T20 only in the collector branch of a transistor T21, since only this branch of the circuit is charged with power. Transistor T21 cooperates with a transistor T19 to form the central unit of multivibrator 13 and the collector of transistor T19 is connected with a resistor R45 whose other end is connected to the unregulated positive supply voltage. The time constant of the monostable multivibrator 13 is determined by the values of a series arrangement of a capacitor C16 and a resistor R47.

At the output of the monostable multivibrator circuit 13 special provisions are made to improve the actuation of the subsequent final stage constituted by pulse amplifier 14. In order to assure minimum current consumption in the circuit, it is important to achieve by means of steep pulse edges a rapid changeover from the blocked to the conductive state and vice versa in the power stage of pulse amplifier 14. With normal monostable multivibrators, however, the switch-off edge of the pulse does not have sufficient steepness. In the illustrated circuit this has the result that the transistor T20 remains conductive for a short time after transistor T21 is blocked. Pulse amplifier stage 14 includes a transistor T22 which is turned on, i.e. rendered conductive, in the usual manner by current supplied to its base via R50 and via R48 and C18 when transistor T20 of monostable multivibrator 13 becomes conductive. However, coupling capacitor C18 has the effect of accelerating the switch-off of transistor T22, so that it is blocked, when transistor T21 becomes conductive even if transistor T20 should remain in the conductive state. This is achieved by dimensioning components R48, R50 and C18 in such a manner that the current through R50 flows primarily into capacitor C18, in order to charge that capacitor, when transistor T21 is conducting, so that there is no longer sufficient current flowing to the base of transistor T22 to keep that transistor in the conductive state. The charge of the capacitor C18 must be sufficient to provide the current through resistor R49 during a recovery time defined by the time constant of C16×R45 R46.

The pulse amplifier 14 includes the transistor T22 and a transistor T23. Transistor T23 is connected in a common base configuration and is actuated by a signal supplied to its emitter by means of a coupling capacitor C19. If C19 is initially charged to the positive potential of the supply voltage via resistor R51 and if transistor T22 then switches through, i.e. becomes conductive, the potential at the emitter of transistor T23 is shifted in the negative direction below the circuit ground potential. Since the base terminal of transistor T23 is connected to ground via resistor R52, this transistor is then switched through and produces a pulse at the output 15 via capacitor C20 with an amplitude which is almost double that of the supply voltage. Fluctuations of the output potential at the connecting terminal 15 are limited by a Zener diode D5.

The power supply 16 contains the battery and a circuit for regulating the supply voltage for stages 2 through 6. This includes a transistor T15 which presents a variable resistance in the usual manner and is controlled by transistors T16 and T17. The base-emitter voltage of transistor T17 serves as the reference value for adjusting the resistance presented by transistor T15 in that transistor T17 effects a comparison between its base-emitter voltage and a reduced voltage produced at the point of connection between resistors R39 and R40 forming a voltage divider between the regulated voltage and ground. The regulated supply voltage is set to such a low value that it lies below the operating voltage of the battery types usually employed in cardiac pacemakers.

The battery serving as the energy source is not shown in FIG. 2. It is connected to the circuit between points 17 and 18.

The circuit shown in FIG. 2 includes a number of components that are not specifically mentioned above. These are all conventional components of the types of stages in which they appear and perform conventional functions in those stages.

Finally, there will be described below various possibilities for varying the operating behavior of cardiac pacemaker circuits according to preferred embodiments of the invention, and in particular in the circuit of FIG. 2, without the individual circuit elements having to change their principal mode of operation. These changes in operating behavior are to be effected, like the changes in mode of operation, either during production of the pacemaker or before implantation, in the implanted state or before reimplantation, with additional switching means, such as remote control devices or the like, being provided if required.

A favorable "programmability" of the circuit states is achieved if the stages are designed so that the components can be switched in or out of the system between a point which is accessible even if the circuit is encapsulated and a point which is accessible in any case, such as the positive operating voltage connection or a ground connection.

In summary, in the described embodiment of the circuit of the present invention, it is possible to change the operating behavior by varying the resistances of certain resistors as shown in the table below. The resistors in question are designated with a solid black dot in FIG. 2. In some cases circuit points which must additionally be brought to the outside are indicated by terminal designations, i.e. 19, 20, 21 and 22.

| Operating parameter | Change made in value of resistor: (direction of change)* | Connecting point |
| --- | --- | --- |
| Input sensitivity | R10 (increasing) | 19 |
| Minimum pulse spacing of the input signals | R30 (increasing) | 20 |
| Refractory period | R35 (increasing) | 22 |
| Asynchronous basic rate during normal operation | R36 (decreasing) | 21 |
| Asynchronous basic rate toward the end of the battery service life | R31 (increasing) | |
| Width of the stimulation pulses at the output | R47 (increasing) | |

-continued

| Operating parameter | Change made in value of resistor: (direction of change)* | Connecting point |
| --- | --- | --- |
| Regulated supply voltage | R40 (increasing) | |

*The direction of change of the respective parameter is indicated with respect to an increasing value of the variated resistor. The values of the resistors may be changed according to the individual needs by selecting the proper value during production or by connecting one or more additional extern resistors to the terminals (connecting points) in parallel to the resistor to be changed in value.

The listed resistors either change voltage-determining resistance conditions, as in the case of resistors R10 and R40, time constants of RC combinations, as for resistors R30, R35, R36 and R47, or the voltage drop across a diode in the forward direction as occurs for resistor R31 with reference to D1. These various ways of varying the operating parameters of the system are made possible in the circuit arrangement according to the invention by the directed separation of functions of the individual component groups so that undesirable interaction between circuit elements is reduced and changes in component values can be made without any adverse effects.

A further result of this separation of functions, which simultaneously increases operational reliability and versatility of the circuit is, for example, that such circuits can be equipped with standard semiconductors since the requirements which they must satisfy are not exceedingly critical.

FIGS. 3a–3e illustrate the time sequences of various modes of operation of the cardiac pacemaker circuit according to the invention. FIGS. 3a to 3c relate to R-wave controlled operation, and FIGS. 3d to 3e relate to P-wave controlled operation. R-wave or P-wave controlled operation depends on the location of the electrode supplying the input signal. P-wave control means that the stimulating pulse is triggered by a ventricle action, while it's the auricle action for R-wave control with the respective electrode locations.

FIGS. 3a and 3d show typical waveforms of a heart signal as it would be recorded on an electrocardiogram. FIGS. 3b and 3e illustrate stimulation pulses occurring during synchronous operation, while FIG. 3c shows stimulation pulses produced during operation in the demand mode.

In the selected illustration it is assumed, for reasons of simplicity, that the illustrated heart pulses were preceded by natural heart activity and that subsequently, within the period covered by each diagram, such heart activity did not occur. In each FIG. 3a to 3e the point in time at which an input pulse is processed by the pacemaker is designated $t_0$.

During synchronous, R-wave controlled operation, the R-peak shown in FIG. 3a actuates a pulse, via preamplifier 2 and trigger stage 3, in the monostable multivibrator 4 so as to set astable multivibrator 6 into a starting state which is immediately followed by the emission of a pulse, as shown in FIG. 3b. As a result of the presence of capacitor C11 at the output of trigger stage 5, the input of multivibrator 6 is blocked for pulses arriving immediately after the R-peak and during the refractory period $T_{refr}$. If pulses of an amplitude that can be detected by trigger stage 3 arrive at the input of preamplifier 2 in a regular sequence, capacitor C9 in trigger stage 5 blocks the input of multivibrator 6 for pulses arriving with a time spacing smaller than $1/f_{max}$. The variation of $T_{refr}$ and $f_{max}$ are two independent means for limiting the "fastest possible action" of the pacemaker when responding to a series of input pulses. These two parameters may be varied individually and it is the narrower condition that is determining the actual operation of the pacemaker, although there is an effect of superposition of the setting of the two parameters, which means that the limitation occurs at a lower frequency if the limits are set close together.

FIG. 3b shows that even if no input pulses are received any longer, the pacemaker continues to emit pulses in the rhythm of the asynchronous basic rate, which pulses are actuated by multivibrator 6.

In the demand mode of operation shown in FIG. 3c, there is no pulse emission during natural heart activity. Nevertheless the astable multivibrator 6 is reset to its starting state whenever such activity occurs so that the time period for the asynchronous basic rate continues to run anew every time. The pulse emitted by this multivibrator circuit each time it is reset to the starting state is suppressed, as described, by the logic circuit in trigger stage 10.

In auricle controlled operation, depicted in FIGS. 3d and 3e, the astable multivibrator 6 is set to its starting state in the same manner as in ventricle controlled operation. However, the input signals appearing at the input of preamplifier 2 are now the heart signals received by the auricle electrode. When such a signal appears, a stimulation pulse is emitted, in this mode of operation of the circuit according to the invention, only after a period of delay v after $t_0$ so that it appears in the ventricle at the physiologically correct time. The refractory period $T_{refr}$ and the maximum pulse frequency $f_{max}$ in this mode of signal processing relate correspondingly to the auricle signals. The refractory period in this case must be dimensioned, for example, so that the pacemaker will not react to its own stimulation pulse even after this pulse has travelled to the auricle electrode with a further time delay.

FIG. 4 illustrates the manner in which the asynchronous basic rate of the cardiac pacemaker circuit according to the invention, i.e. the rate of emission of stimulation pulses for the case where no signals from the heart are received, is influenced by the decrease in battery voltage with time according to the discharge characteristic of the battery. The diagram shown in FIG. 4 is based on an assumed discharge curve. In the circuit according to the invention, the illustrated curve is set for two different points of the curve, i.e. either for A and B or for A' and B. The curve path containing points A and B represents the frequency dependence for the case in which the circuit which determines the basic rate, i.e. multivibrator 6 is supplied by an unregulated voltage source, while the curve containing points A' and B shows the same dependence for the case of a regulated voltage supply, which is the case for the circuit illustrated in FIG. 2.

With an unregulated voltage supplying the circuit determining the basic rate, this rate is set so that point A, representing the basic rate for the major portion of the period of operation, is disposed in the almost horizontal region of the curve. In this region of the curve the frequency changes but slightly since the operating voltage of the battery also remains almost constant. Adaptation to the type of battery involved is effected by adapting the basic rate precisely to the respective voltage value so that it is able to take on the same value for all pacemaker types with all types of batteries.

Regarding the curve through A' and B for the case of a regulated voltage supply, the supply voltage is fixed independently of the type of battery, to the voltage curve shown by the straight horizontal line, so that individual adaptation to the respective type of battery is not necessary.

In the course of aging of the energy source, here the battery, its voltage becomes progressively lower. This decrease in voltage becomes steeper with increasing exhaustion. With a regulated voltage supply there then occurs the case, at point C of FIG. 4, that the regulation is no longer effective since the voltage at the input of the regulating member approximates the output voltage. From point C of the curve, both a regulated and an unregulated voltage exhibit the same behavior.

In the circuit according to the invention, means are provided which make it possible to additionally set a given frequency for a given voltage value in the descending range of the curve so as to indicate to the treating physician or to the patient, with the aid of a suitable measuring device, that the exhaustion of the energy source has advanced to a certain degree. Since the curve shown in FIG. 4 can be influenced by two separate, adaptable parameters, the curve path can be set for all of the various embodiments of pacemakers provided with a circuit according to the invention so that the values indicating a certain degree of aging of the energy source will be the same. The necessary monitoring devices can thus be of uniform construction and the measurements can easily be made without requiring switching.

In addition, the circuit according to the invention also provides the possibility of making the frequency variation curve steeper in the descending region beyond point C in order to indicate the impending exhaustion of the energy source with even greater certainty and thus further reduce the risk for the patient. For this purpose diode D1 is provided in the astable multivibrator 6 shown in FIG. 2. As soon as the ratio of its almost constant forward voltage to the supply voltage of the multivibrator 6, which is decreasing at a progressive rate, exceeds a certain value, the charging time of capacitor C10 is overproportionately increased via R36 and due to R36·C10 >> R35·C12 the pulse rate in asynchronous operation is correspondingly reduced overproportionately. R31 is used to vary the forward voltage of D1 and thus the onset of the increased steepness of the slope so that the curve of the asynchronous basic rate passes, as described, through the given point B.

The illustrated embodiment represents only one of many ways of realizing a pacemaker circuit according to the invention. Other circuits are possible which additionally permit a P-wave inhibiting mode of operation. One the other hand, with some additional electronic components, circuits can be realized which automatically change, depending on the operating requirements, from the ventricle controlled to the auricle controlled mode, and vice versa. But even a possibility for external switching by means of a Reed relay or the like permits changing of the pacemaker, for example in the case of the auricle electrode becoming displaced, to ventricle controlled operation without having to explant the pacemaker, thereby assuring further reliable stimulation of the patient's heart.

The resulting universal applicability of the pacemaker circuit makes it possible as well to operate the circuit with different types of batteries at different operating voltages, depending on the application involved.

This characteristic of the circuit is explained by the fact that the pulse shaping means employed in any one of the modes of operation assure dependable operation under all conditions. Since the individual component groups are substantially decoupled, the refractory period, for example, is independent of the shape of the input signal and the like. The apparent additional expenditures for the additional components are more than compensated by the multitude of advantages realized by the present invention so that the circuit according to the invention is of advantage in almost all cases and thus represents, in the long run, a more economical solution.

Listing of Components

| Resistors: | | | Capacitors: | |
|---|---|---|---|---|
| R 1 | | 22 k | C 1 | 33 μF |
| R 2 | | 8.2 M | C 2 | 10 n |
| R 3 | | 8.2 M | C 3 | 2.2 n |
| R 4 | | 8.2 M | C 4 | 22 n |
| R 5 | | 47 k | C 5 | 470 p |
| R 6 | | 5.6 M | C 6 | 470 p |
| R 7 | | 5.6 M | C 7 | 4.7 n |
| R 8 | | 1.8 M | C 8 | 2.2 n |
| R 9 | | 10 k | C 9 | 10 n |
| R 10 | about | 100 k | C 10 | 68 n |
| R 11 | | 3.3 M | C 11 | 22 n |
| R 12 | | 10 M | C 12 | 10 n |
| R 13 | | 10 k | C 13 | 33 μF |
| R 14 | | 10 M | C 14 | 1 n |
| R 15 | | 3.9 M | C 15 | 100 p |
| R 16 | | 3.9 M | C 16 | 220 p |
| R 17 | | 10 M | C 17 | 100 p |
| R 18 | | 10 M | C 18 | 22 n |
| R 19 | | 3.9 M | C 19 | 33 μF |
| R 20 | | 190 k | C 20 | 3.3 μF |
| R 21 | | 22 M | | |
| R 22 | | 470 k | Transistors: | |
| R 23 | | 680 k | | |
| R 24 | | 3.9 M | T 1 | 2 N 7939 |
| R 25 | | 3.9 M | T 2 | 2 N 7939 |
| R 26 | | 1 M | T 3 | 2 N 7939 |
| R 27 | | 10 M | T 4 | 2 N 7609 |
| R 30 | about | 3.9 M | T 5 | 2 N 7939 |
| R 31 | about | 1 k | T 6 | 2 N 7609 |
| R 32 | | 10 M | T 7 | 2 N 7939 |
| R 33 | | 680 k | T 8 | 2 N 7939 |
| R 34 | | 1 k | T 9 | 2 N 7609 |
| R 35 | about | 10 M | T 10 | 2 N 7939 |
| R 36 | about | 10 M | T 11 | 2 N 7939 |
| R 37 | | 2.2 M | T 12 | 2 N 7609 |
| R 38 | | 10 M | T 13 | 2 N 7609 |
| R 39 | | 10 M | T 14 | 2 N 7939 |
| R 40 | about | 2.2 M | T 15 | 2 N 7609 |
| R 41 | | 22 M | T 16 | 2 N 7939 |
| R 42 | | 1 M | T 17 | 2 N 7939 |
| R 43 | | 10 M | T 18 | 2 N 7939 |
| R 44 | | 10 M | T 19 | 2 N 7939 |
| R 45 | | 5.6 M | T 20 | 2 N 7609 |
| R 46 | | 270 k | T 21 | 2 N 7939 |
| R 47 | about | 3.9 M | T 22 | 2 N 7610 |
| R 48 | | 39 k | T 23 | 2 N 7610 |
| R 49 | | 3.9 M | | |
| R 50 | | 33 k | Diodes: | |
| R 51 | | 33 K | | |
| R 52 | | 15 k | D 1 | 1 N 4148 |
| R 53 | | 33 k | D 2 | 1 N 4148 |
| R 54 | | 33 k | D 3 | 1 N 4148 |
| | | | D 4 | 1 N 4148 |
| | | | D 5 | Z 8.2 |
| Switch: | | | D 6 | 1 N 4148 |
| S 1 | | reed-switch | D 7 | 1 N 4148 |

Supply voltage between 1.8 and 5.5 volts

It will be understood that the above description of the present invention is susceptible to various modifications, changes and adaptations, and the same are intended to be comprehended within the meaning and range of equivalents of the appended claims.

What is claimed is:

1. An artificial cardiac pacemaker circuit connected to operate selectively in either one of two different modes of operation, comprising:

electrode means implantable in the heart of a patient for receiving heart signals produced thereby and supplying heart stimulation pulse signals thereto;

a first pulse generator having an input connected to said electrode means for generating a pulse having a predetermined duration in response to each signal appearing at said electrode means; and a second pulse generator including an input connected to the output of said first pulse generator, an output connected to said electrode means for supplying heart stimulation pulses thereto, means defining a first signal path connected to actuate a signal at said output of said second pulse generator in response to the start of each output pulse produced by said first pulse generator, and to actuate a signal at said output of said second pulse generator at the end of a given interval during which no output pulse is produced by said first generator, the given interval being longer than the duration of each output pulse produced by said first generator, means defining a second signal path connected to provide in response to each output pulse produced by said first pulse generator, a signal having a duration corresponding to the duration of said output pulse, connection means connected between at least one of said signal paths and said output of said second pulse generator and connectable for establishing a selected one of a first connection configuration in which each signal appearing in said first signal path generates a heart stimulation pulse at said output of said second pulse generator, and a second connection configuration, and signal responsive means connected to said connection means when said connection means is connected in said second connection configuration for preventing the appearance of a heart stimulation pulse at said output of said second pulse generator during the time when a signal is present in said second signal path.

2. An artificial cardiac pacemaker circuit connected to operate selectively in either one of two different modes of operation, comprising:

electrode means implantable in the heart of a patient for receiving heart signals produced thereby and supplying heart stimulation pulses thereto;

a first pulse generator having an input connected to said electrode means for generating a pulse having a predetermined duration in response to each heart signal received by said electrode means; and a second pulse generator including an input connected to the output of said first pulse generator, an output connected to said electrode means for supplying heart stimulation pulses thereto, means defining a first signal path connected to said second pulse generator input, generating means connected between said first signal path and said output of said second pulse generator for causing said second generator to produce a signal in response to the start of each output pulse produced by said first pulse generator, and to produce a signal at the end of a given interval during which no output pulse is produced by said first generator, means defining a second signal path connected to provide a signal having a duration shorter than said given interval in response to each output pulse produced by said first pulse generator, and connection means connected between said second signal path and said output of said second pulse generator and connectable for establishing a selected one of a first connection configuration in which said second signal path is blocked and said generating means responds to each signal appearing in said first signal path to generate a heart stimulation pulse at said output of said second pulse generator means and a second connection configuration in which said second signal path is unblocked and the generation of a heart stimulation pulse at said electrode means in response to each signal appearing in said first signal path is prevented during occurrence of a signal provided by said second signal path.

3. An artificial cardiac pacemaker circuit connected to operate selectively in either one of two different modes of operation, comprising:

electrode means implantable in the heart of a patient for receiving heart signals produced thereby and supplying heart stimulation pulse signals thereto;

a first pulse generator having an input connected to said electrode means for generating a pulse having a predetermined duration in response to each signal appearing by said electrode means; and a second pulse generator including an input connected to the output of said first pulse generator, an output connected to said electrode means for supplying heart stimulation pulses thereto, means defining a first signal path connected to actuate a signal at the output of said second pulse generator in response to the start of each output pulse produced by said first pulse generator, means defining a second signal path connected to provide, in response to each output pulse produced by said first pulse generator, a signal which is delayed by a period relative to the start of each output pulse produced by said first pulse generator, and connection means connected between said signal paths and said output of said second pulse generator and connectable for establishing a selected one of a first connection configuration in which it connects said first signal path to said output of said second pulse generator for causing each signal appearing in said first signal path to generate a heart stimulation pulse at said electrode means and a second connection configuration in which it connects said second signal path to said output of said second pulse generator for causing each signal appearing in said second signal path to generate a heart stimulation pulse at said electrode means.

4. Circuit as defined in claim 1, 2 or 3 wherein at least one of said pulse generators comprises at least one multivibrator device.

5. Circuit as defined in claim 4 wherein said electrode means are arranged for deriving an input signal from the heart of an individual using said pacemaker, wherein said multivibrator device is connected to be triggered by such input signal in order to begin emission of a pulse in response to said input signal.

6. Circuit as defined in claim 5 wherein said multivibrator device is an astable multivibrator device which emits pulses at a given repetition rate always starting from the last pulse emitted in response to a said input signal.

7. Circuit as defined in claim 1, 2, or 3 wherein one of said generators comprises means for fixing the time of the emission of the stimulation pulses, and said second generator comprises means for giving each stimulation pulse a certain time duration.

8. Circuit as defined in claim 7 wherein said means for fixing the point in time at which stimulation pulses are emitted comprise an astable multivibrator device.

9. Circuit as defined in claim 7 wherein said first pulse generator comprises a monostable multivibrator device.

10. Circuit as defined in claim 1, 2 or 3 wherein one of said pulse generators comprises an astable multivibrator constructed to operate between end states having respectively different durations and composed of a transistor having base, emitter, and collector electrodes, circuit components for setting the duration of the longer duration state, said components being connected to said transistor base, and a diode connected in the collector-emitter path of said transistor and poled to conduct in its forward direction.

11. Circuit as defined in claim 10 wherein one of said collector and emitter of said transistor constitutes an output electrode and said multivibrator further comprises a resistor connected to said output electrode and having a resistance value which influences the repetition rate of the pulses produced by said multivibrator.

12. Circuit according to claim 1, 2 or 3 further comprising means including a battery for supplying different operating voltages to said circuit and voltage regulating means producing a regulated supply voltage for one of said pulse generators, which regulated voltage is below the value of the lowest battery voltage occurring during normal battery service life.

13. Circuit as defined in claim 12 wherein said voltage regulating means are constituted by a transistorized voltage regulator device.

14. Circuit as defined in claim 1, 2 or 3 wherein one of said pulse generators comprise an astable multivibrator arranged to produce spaced output pulses and having a control input connected to receive a trigger signal which causes said multivibrator to produce an output pulse, and further comprising blocking means including a capacitor connected to said multivibrator to be charged during production of each output pulse and discharged at a selected rate after the end of each output pulse, said capacitor blocking production of pulses by said multivibrator during a fixed portion of each discharge of said capacitor for blocking the input of said multivibrator with respect to triggering signals which occur within a selected time after a trigger signal which causes said multivibrator to produce an output pulse.

15. Circuit as defined in claim 14 wherein said blocking means further comprise a diode connected between said capacitor and a point at fixed potential and poled to conduct in its forward direction in order to effect charging of said capacitor.

16. Circuit as defined in claim 14 wherein said blocking means further comprise a resistor connected between said capacitor and a point at fixed potential and providing a discharge path for said capacitor.

17. Circuit as defined in claim 16 wherein said resistor has a variable resistance whose value determines the rate of discharge of said capacitor.

18. Circuit as defined in claim 14 wherein said multivibrator further comprises a resistor connected between one side of said capacitor and said multivibrator control input.

19. Circuit as defined in claim 1, 2 or 3 further comprising output means connected, during operation in at least connection configuration, to produce a heart stimulation pulse in response to each pulse emitted by said second pulse generator, said output means comprising a multivibrator device and a pulse amplifier device, said multivibrator device containing a push-pull final stage composed of two active components and means alternately rendering said active components conductive in response to each pulse emitted by said second pulse generator while permitting said active components to be temporarily simultaneously conductive, each active component having a separate output, said pulse amplifier device being connected to said outputs to be actuated when one of said active components becomes conductive and to be deactuated when the other one of said active components becomes conductive, and said multivibrator device further including a resistor connecting the output of said one active component to said pulse amplifier device and a capacitor connecting the output of said other active component to said pulse amplifier device.

20. Circuit as defined in claim 19 wherein said multivibrator device further comprises a further resistor connected between said two active components.

21. Circuit as defined in claim 1 wherein said means defining a second signal path are arranged to actuate a signal at the output of said second pulse generator upon termination of a signal provided by said second signal path, and said connection means are arranged for interrupting said second signal path in said first connection configuration and said first signal path in said second connection configuration.

22. Circuit as defined in claim 21 wherein the duration of each signal provided by said second signal path corresponds substantially to the period of delay between the P-wave and the R-wave in the natural excitation behavior of a human heart.

23. Circuit as defined in claim 2 wherein said second pulse generator comprises a logic conjunction circuit which, when said connection means establishes said second configuration, causes said second pulse generator to provide a heart stimulation pulse at its output upon the appearance of a signal in said first signal path and the simultaneous absence of a signal in said second signal path.

24. Circuit as defined in claim 1, 2 or 3 wherein one of said pulse generators comprises an oscillator whose operating frequency is dependent on its supply voltage such that the change in its operating frequency as a function of a change in its supply voltage increases near the end of the operating life of the voltage supply of said circuit.

25. Circuit as defined in claim 24 wherein the operating frequency of said oscillator decreases with decreases in its supply voltage.

26. Circuit as defined in claim 1 wherein said signal responsive means comprises a logic conjunction circuit which, when said connection means establishes said second configuration, causes said second pulse generator to provide a heart stimulation pulse at its output upon the appearance of a signal in said first signal path and the simultaneous absence of a signal in said second signal path.

* * * * *